US012727939B2

(12) United States Patent
Kim

(10) Patent No.: US 12,727,939 B2
(45) Date of Patent: Sep. 8, 2026

(54) DEVICES AND METHODS FOR TREATING LUNG TUMORS

(71) Applicant: June Hong Kim, Busan (KR)

(72) Inventor: June Hong Kim, Busan (KR)

(73) Assignees: TAU MEDICAL INC., Busan (KR); PUSAN NATIONAL UNIVERSITY TECHNOLOGY HOLDINGS CO., LTD., Busan (KR)

( * ) Notice: Subject to any disclaimer, the term of this patent is extended or adjusted under 35 U.S.C. 154(b) by 257 days.

(21) Appl. No.: 18/218,987

(22) Filed: Jul. 6, 2023

(65) Prior Publication Data

US 2024/0008919 A1 Jan. 11, 2024

Related U.S. Application Data

(60) Provisional application No. 63/358,806, filed on Jul. 6, 2022.

(51) Int. Cl.

| | |
|---|---|
| ***A61B 18/14*** | (2006.01) |
| ***A61B 1/00*** | (2006.01) |
| ***A61B 1/015*** | (2006.01) |
| ***A61B 1/018*** | (2006.01) |
| ***A61B 1/267*** | (2006.01) |
| ***A61B 18/00*** | (2006.01) |

(52) U.S. Cl.

CPC ...... *A61B 18/1492* (2013.01); *A61B 1/00082* (2013.01); *A61B 1/015* (2013.01); *A61B 1/018* (2013.01); *A61B 1/2676* (2013.01); *A61B 2018/00535* (2013.01); *A61B 2018/00541* (2013.01); *A61B 2018/00577* (2013.01)

(58) Field of Classification Search

CPC . A61B 18/1492; A61B 1/00082; A61B 1/015; A61B 1/018; A61B 1/2676; A61B 2018/00535; A61B 2018/00541; A61B 2018/00577

See application file for complete search history.

(56) References Cited

U.S. PATENT DOCUMENTS

2002/0058884 A1* 5/2002 Burbank ................ A61B 90/39 600/564

2019/0343581 A1* 11/2019 Panescu ............. A61B 18/1492

OTHER PUBLICATIONS

"Medical Applications and Toxicities of Gallium Compounds", Christopher R. Chitambar, May 10, 2010, International Journal of Environmental Research and Public Health, vol. 7, p. 2337-2361 (Year: 2010).*

* cited by examiner

*Primary Examiner* — Linda C Dvorak
*Assistant Examiner* — Abigail Bock
(74) *Attorney, Agent, or Firm* — Justin H. Kim

(57) ABSTRACT

An RF (radiofrequency) ablation catheter device having a flexible shaft, a distal end, an inflatable balloon mounted on the shaft, having a portion of the flexible shaft that is distal to the inflatable balloon and an RF electrode located on the distal segment of the shaft. A device and method of treating a tumor in a patient having a liquid conductive material, inserting an ablation catheter device into a body organ, advancing the ablation catheter device to a passageway at a target site in the body organ, instilling a volume of the liquid conductive material into the passageway; and applying an RF current to the liquid conductive material.

11 Claims, 16 Drawing Sheets

Length of the cone-shaped LM = 30 mm

FIG. 12B

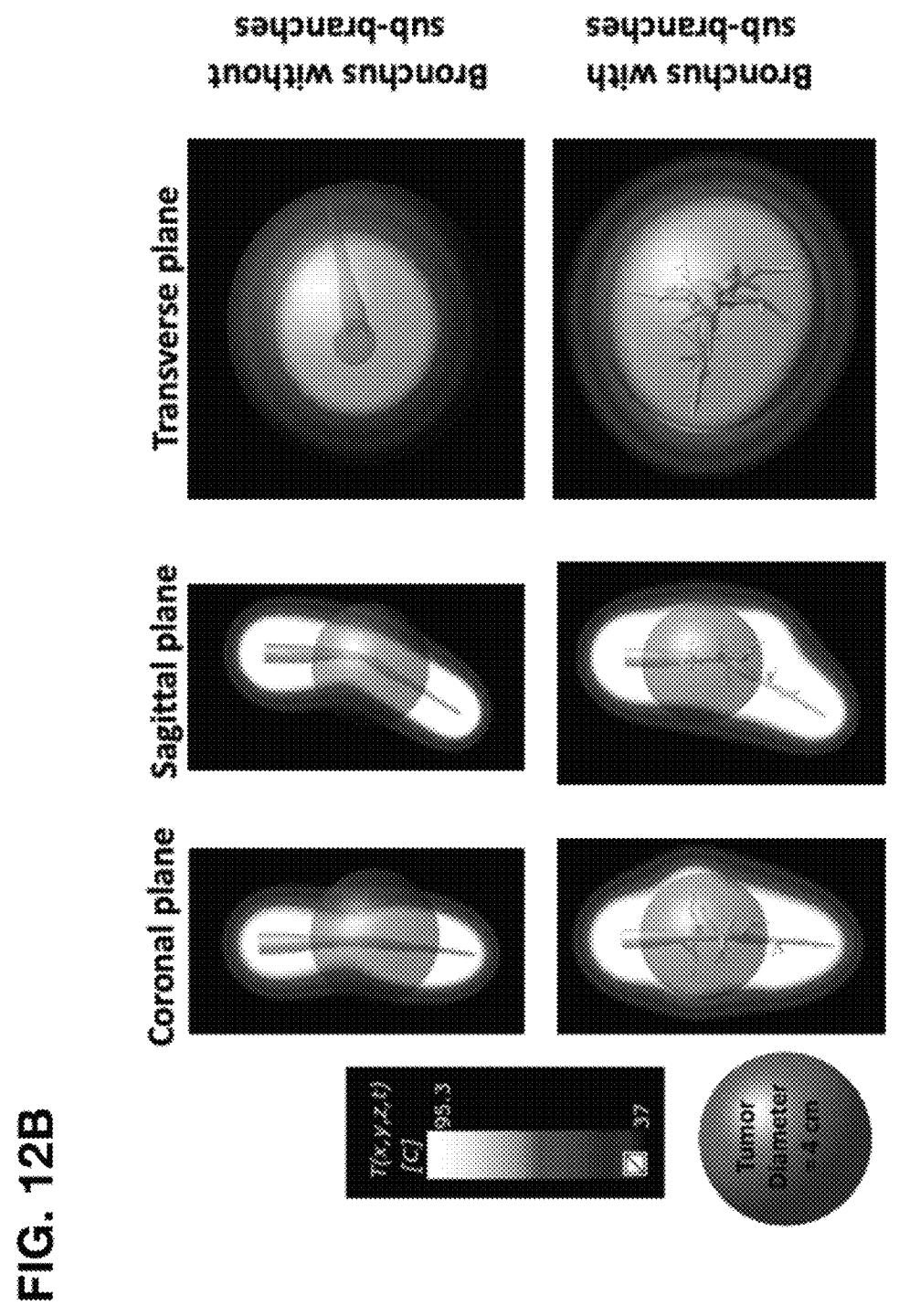

Transverse plane

Sagittal plane

Coronal plane

Bronchus without sub-branches

Bronchus with sub-branches

T(x,y,z,t) [C]

95.3

37

Tumor Diameter : 4 cm

DEVICES AND METHODS FOR TREATING LUNG TUMORS

The present application claims the benefit of U.S. Provisional Application No. 63/358,806, filed Jul. 6, 2022; all of which is incorporated herein by reference.

TECHNICAL FIELD

The present disclosure is directed generally to devices and methods for ablating malignant lung tumors and more particularly the treatment of peripheral lung tumors by using liquid conductive metal as electrodes.

BACKGROUND

Various radiofrequency ablation (RFA) has been utilized for treating peripheral lung tumors. However, there remains a need for improvement due to insufficient ablation coverage and the difficulty of endoscopically navigating the ablation electrodes to targeted tumors in the peripheral pulmonary lesions (PPL). It is desired for the ablation electrodes to be flexible and relatively soft and fit in the PPL that is small in diameter, preferable less than 2 mm, in order to ablate tumors that are closer to the peripheral of the lung.

SUMMARY

The above limitation is solved by using bronchial branches in the PPL as electrodes by filling the branches with liquid metal (i.e., eGaIn), isolating within the branches with the occlusion balloon, and applying an RF current to the isolated liquid metal in the branches. Accordingly, the enclosed liquid metal within the branches acts as RF electrodes so that the tumors within the branches are sufficiently ablated. After the ablation, the liquid metal is removed by suction.

BRIEF DESCRIPTION OF THE DRAWINGS

FIG. 12B shows comparison results depending on whether the sub-branches exist or not.

DESCRIPTION OF EXAMPLE EMBODIMENTS

To assist in understanding the invention, reference is made to the accompanying drawings to show by way of illustration specific embodiments in which the invention may be practiced. The drawings herein are not necessarily made to scale or actual proportions. For example, the lengths and widths of the components may be adjusted to accommodate the page size.

Ablation Catheter

Figures 1A, 1B:
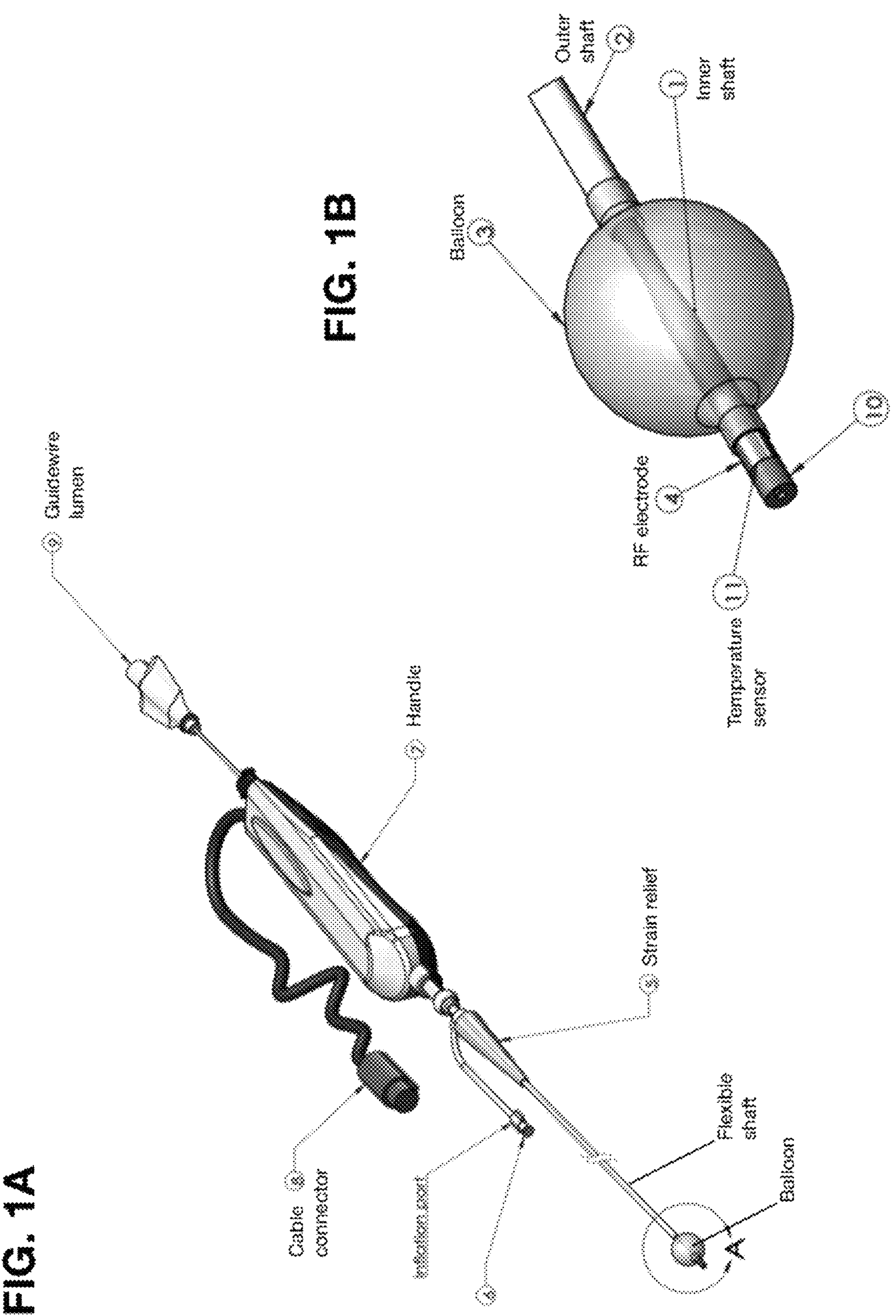
FIGS. 1A-1B shows the ablation catheter device.

FIG. 1A shows the ablation catheter device. The device comprises a flexible shaft having a length of 50-250 cm, and a distal end. The device further comprises an inflatable balloon mounted on the shaft at a location that is within 3 cm of the distal end of the shaft. A portion of the flexible shaft that is distal to the inflatable balloon is defined as a distal segment of the shaft. The device further comprises an RF electrode located on the distal segment of the shaft.

In some embodiments, the RF electrode is located within a 1.5 cm distance from the inflatable balloon. In some embodiments, the distal segment of the shaft has a length of less than 2.0 cm.

Figure 2A:
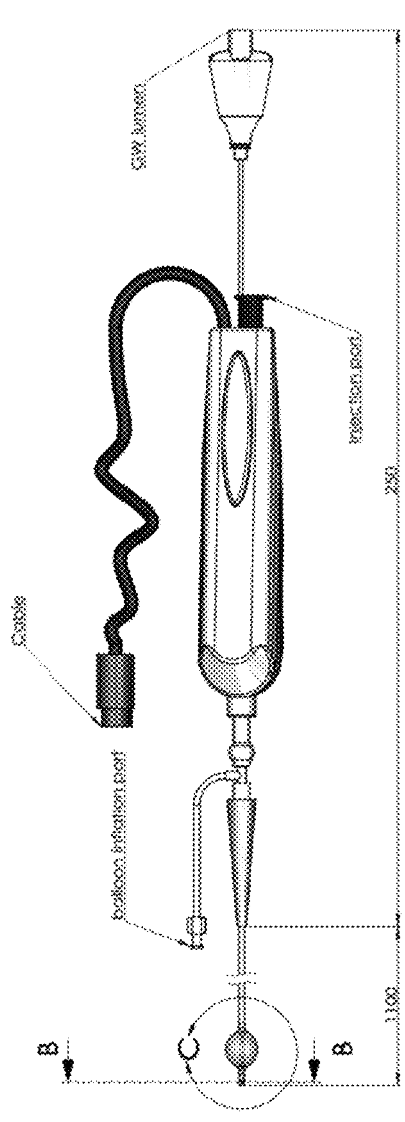
FIGS. 2A-2C shows the ablation catheter device more in detail.
Figure 2C:
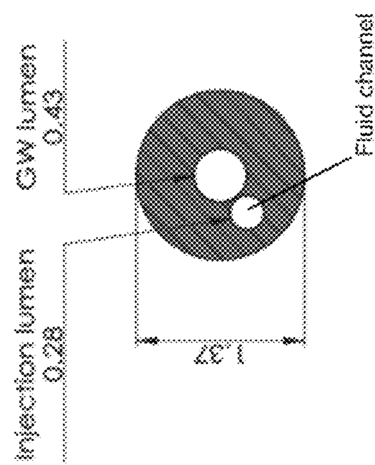

The flexible shaft further comprises a fluid channel as shown in FIG. 2C. The flexible shaft further comprises an injection port that is in communication with the fluid channel of the flexible shaft as shown in FIG. 2A. The fluid channel has a fluid volume that is less than 1.5 ml.

Figure 2B:
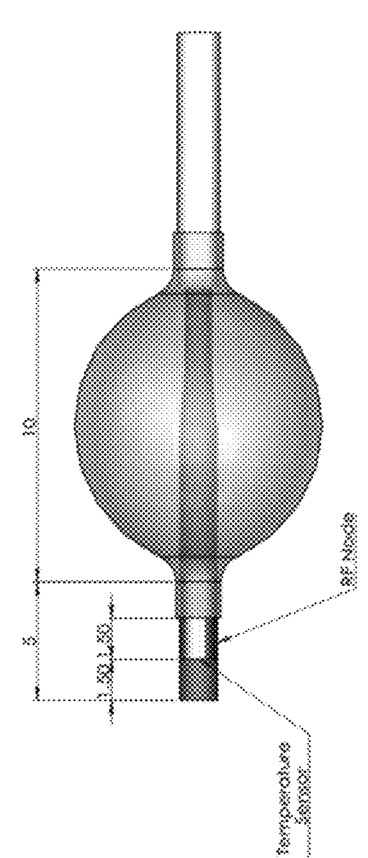

The ablation catheter further comprises a temperature sensor mounted on the distal segment of the shaft as shown in FIG. 2B.

Ablation Catheter Assembly

Figure 3:
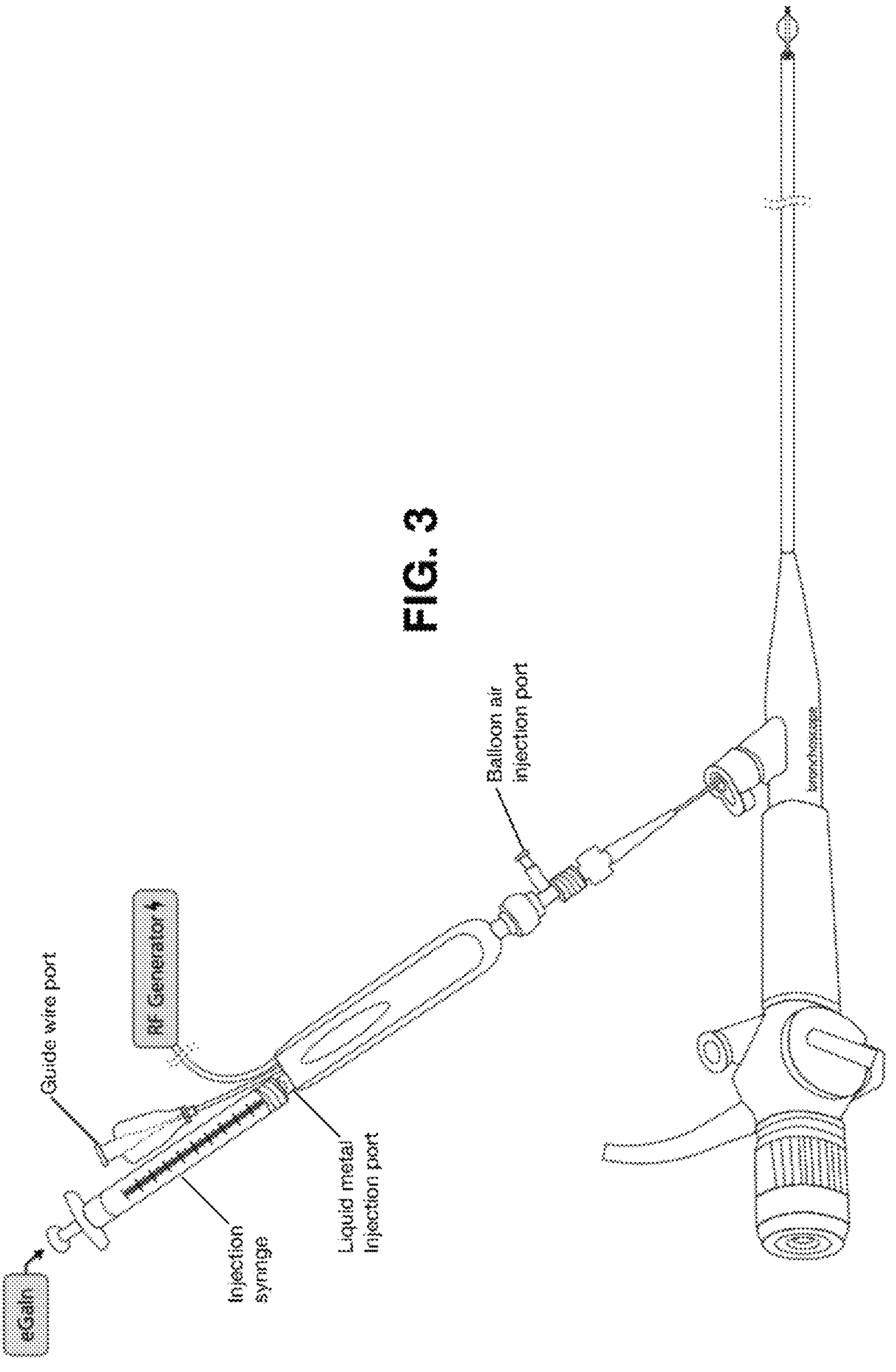
FIG. 3 shows the ablation catheter assembly.
Figure 4:
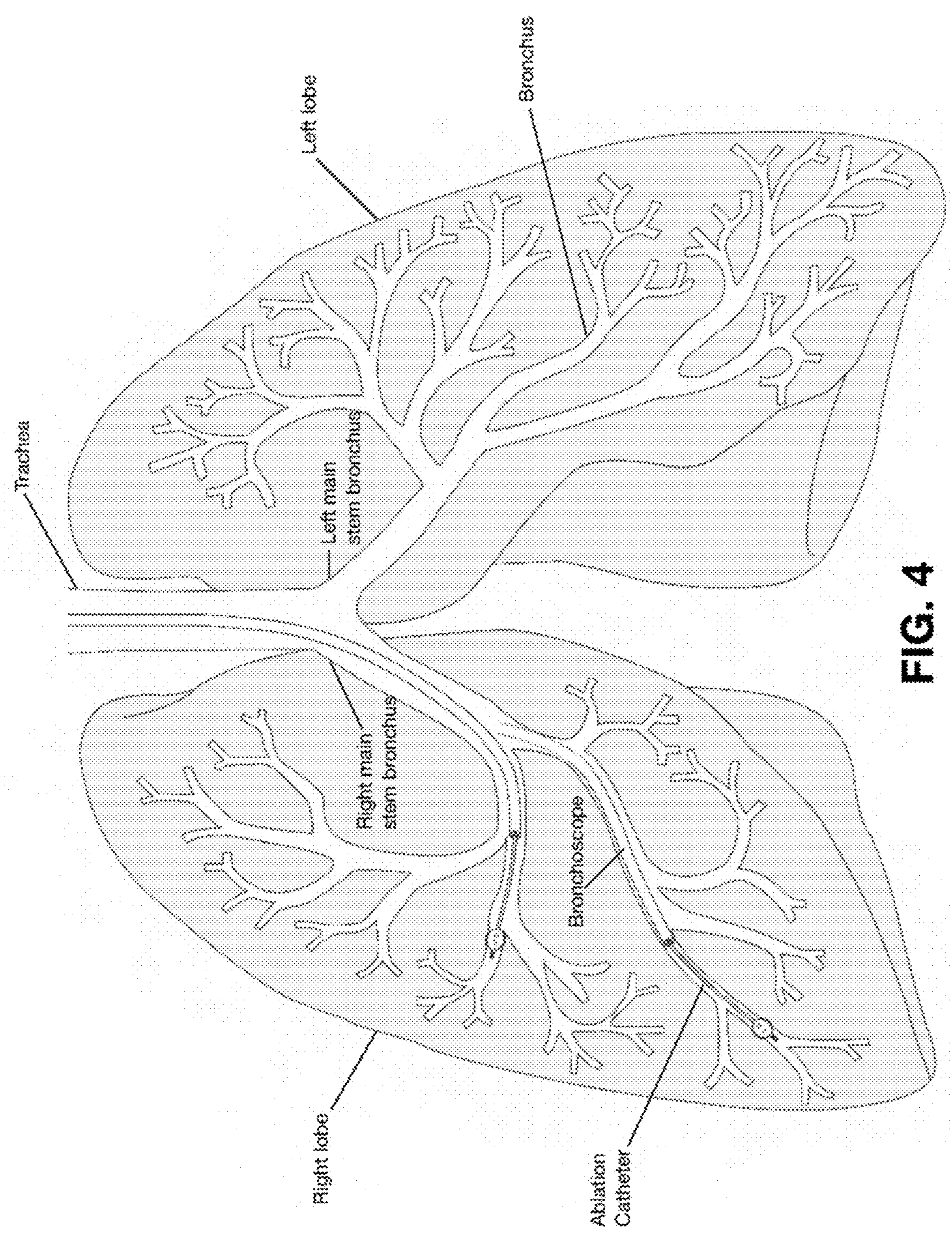
FIG. 4 shows the ablation catheter assembly placed in the lung.

Another aspect of the invention is an ablation assembly, which comprises an ablation catheter (as described herein) and a flexible bronchoscope as shown in FIG. 3. The bronchoscope may comprise an instrument channel (working channel) and/or a fluid channel. The ablation catheter is configured to travel through the instrument channel of the bronchoscope. For example, FIG. 4 shows the ablation catheter is positioned at a target site through the bronchoscope in the lung.

The ablation assembly may further comprise an injection syringe containing the liquid conductive material as shown in FIG. 3. The injection syringe is connected to the injection port of the ablation catheter. The amount of liquid conductive material contained in the syringe may be less than 2.0 ml; in some cases, less than 1.0 ml; and in some cases, less than 0.5 ml. The syringe contains at least 0.1 ml of the liquid conductive material.

In some embodiments, the ablation assembly further comprises an RF generator that is electrically coupled to the ablation catheter.

Aspiration of the conductive liquid material out of the airway may be done by suction through the injection lumen and/or guidewire lumen of the ablation catheter as shown in FIG. 2C, or by the bronchoscope (e.g., suction through the instrument/working channel or the fluid channel).

In some embodiments, the bronchoscope has a diameter of less than 4.0 mm. The bronchoscope further comprises a fluid channel for instilling or suctioning fluid.

The ablation catheter device further comprises an injection port as shown in FIGS. 2A and 3. The assembly further comprises an injection syringe containing a liquid conductive material as shown in FIG. 3. In some embodiments, the liquid conductive material has a volume of less than 2.0 ml.

In some embodiments, the liquid conductive material contains essentially no saline or water.

Ablation Treatments

Figure 9:
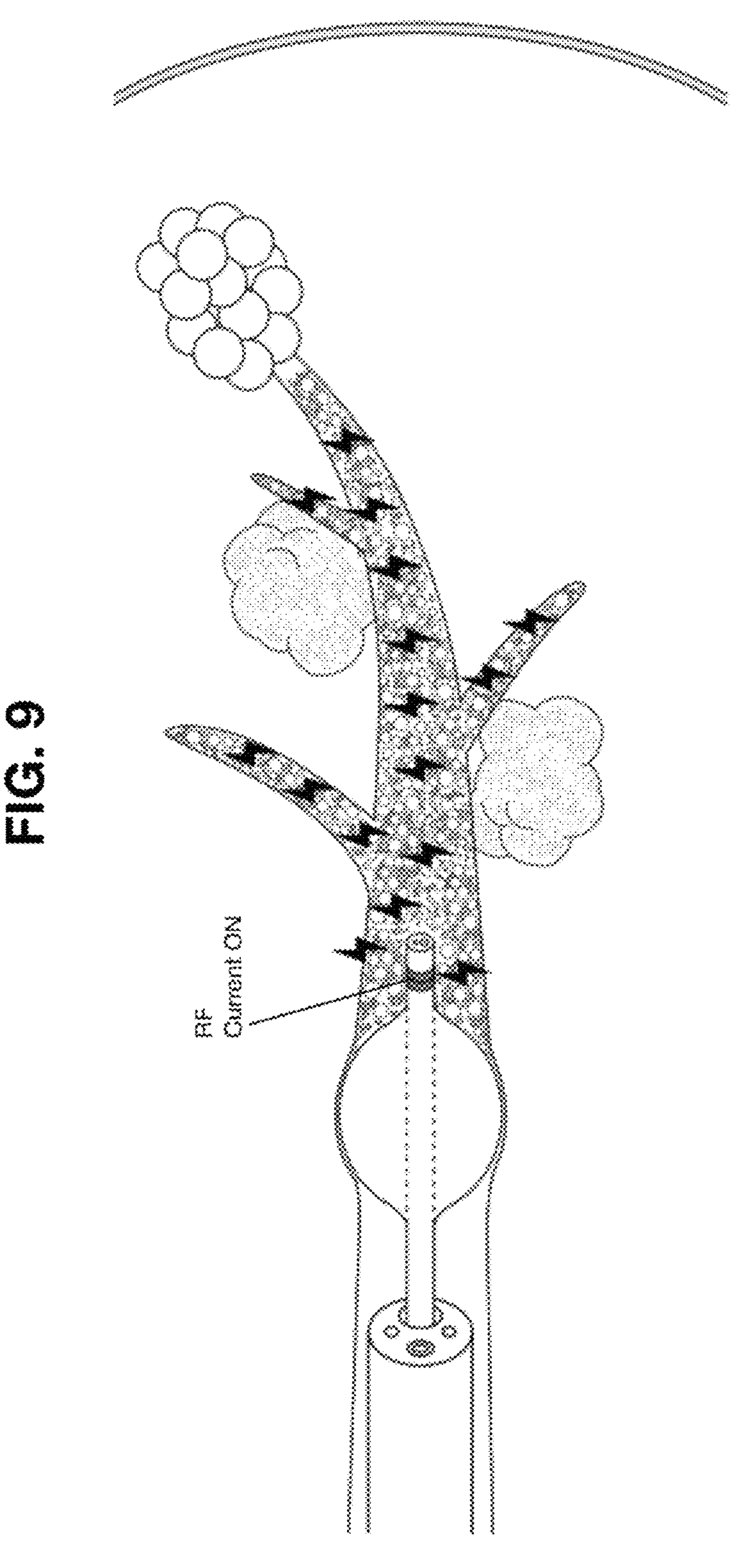
FIG. 9 shows the step of applying the RF current to the liquid metal.
Figures 10A, 10B:
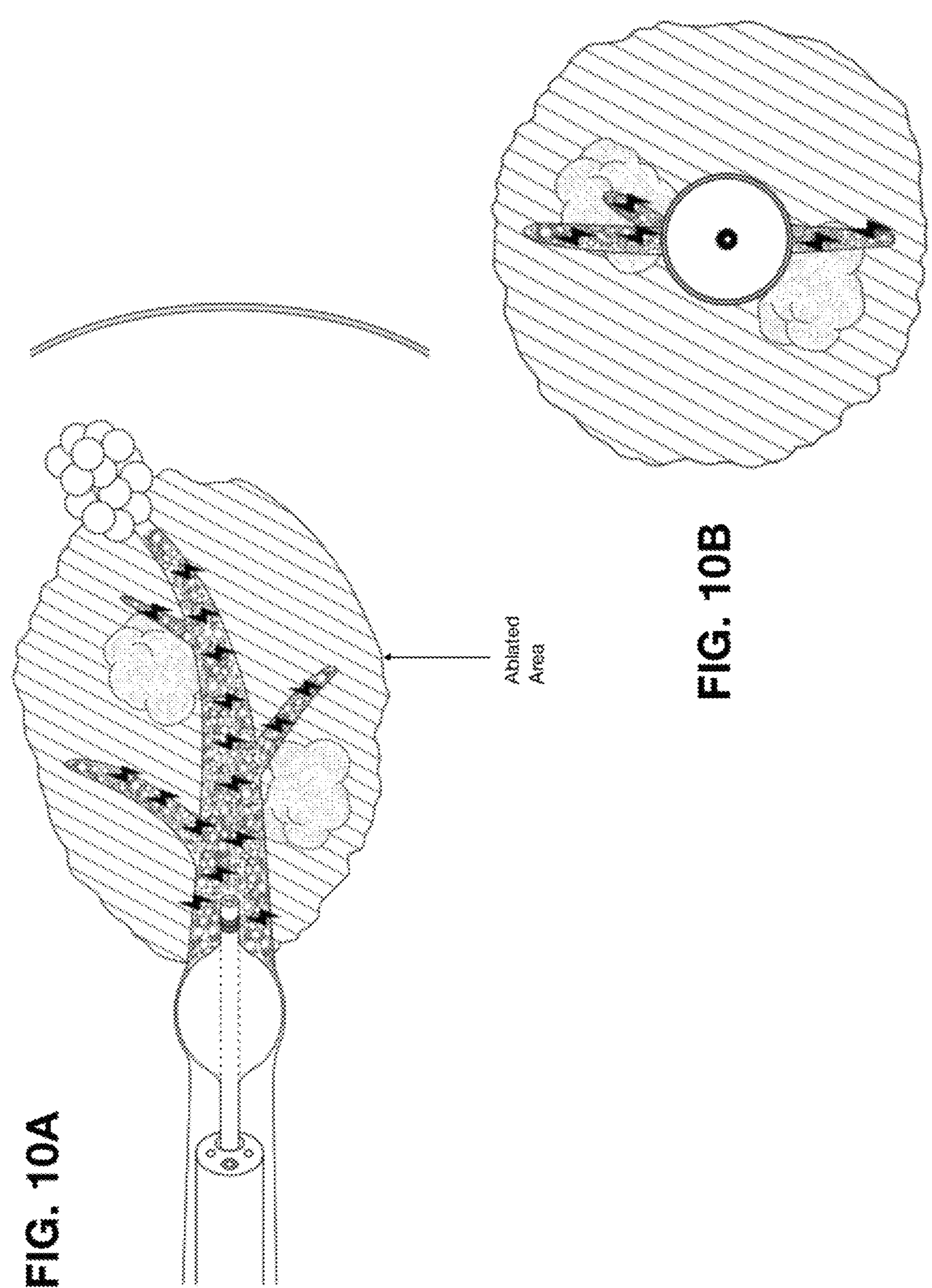
FIGS. 10A-10B shows the situation where the target zone is being ablated.

The method of treating a tumor in a patient may comprise:

1. Having the liquid conductive material that comprises gallium;
2. Inserting the ablation catheter device into a body organ (FIGS. 6A-6B);
3. Advancing the ablation catheter device to a passageway at a target site in the body organ (FIGS. 6A-6B);
4. Instilling a volume of the liquid conductive material into the passageway (FIGS. 7A-7B); and
5. Applying an RF current to the liquid conductive material (FIG. 9).

Figures 7A, 7B:
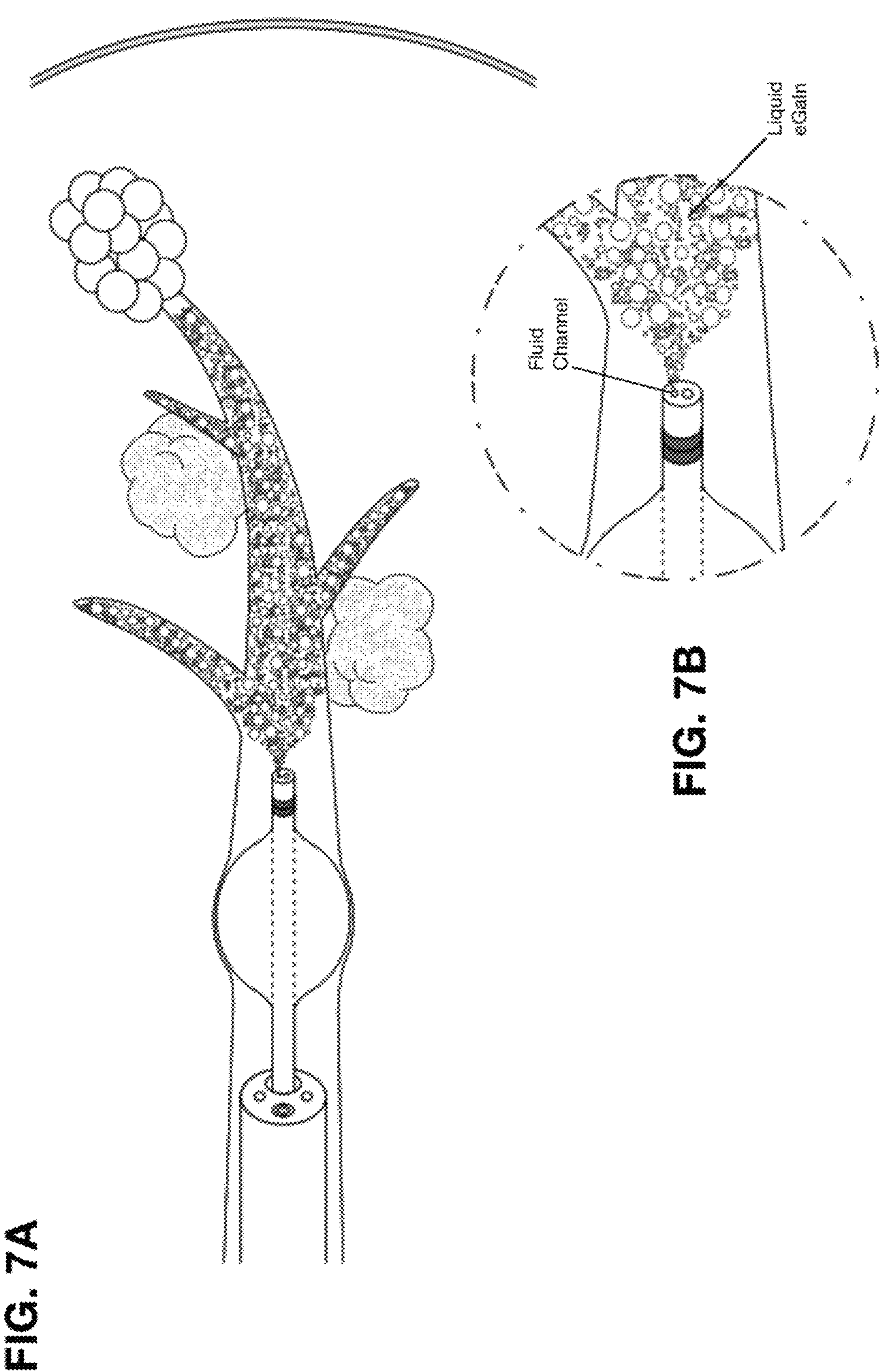
FIGS. 7A-7B shows the steps of instilling the liquid metal into the target branches.
Figure 8:
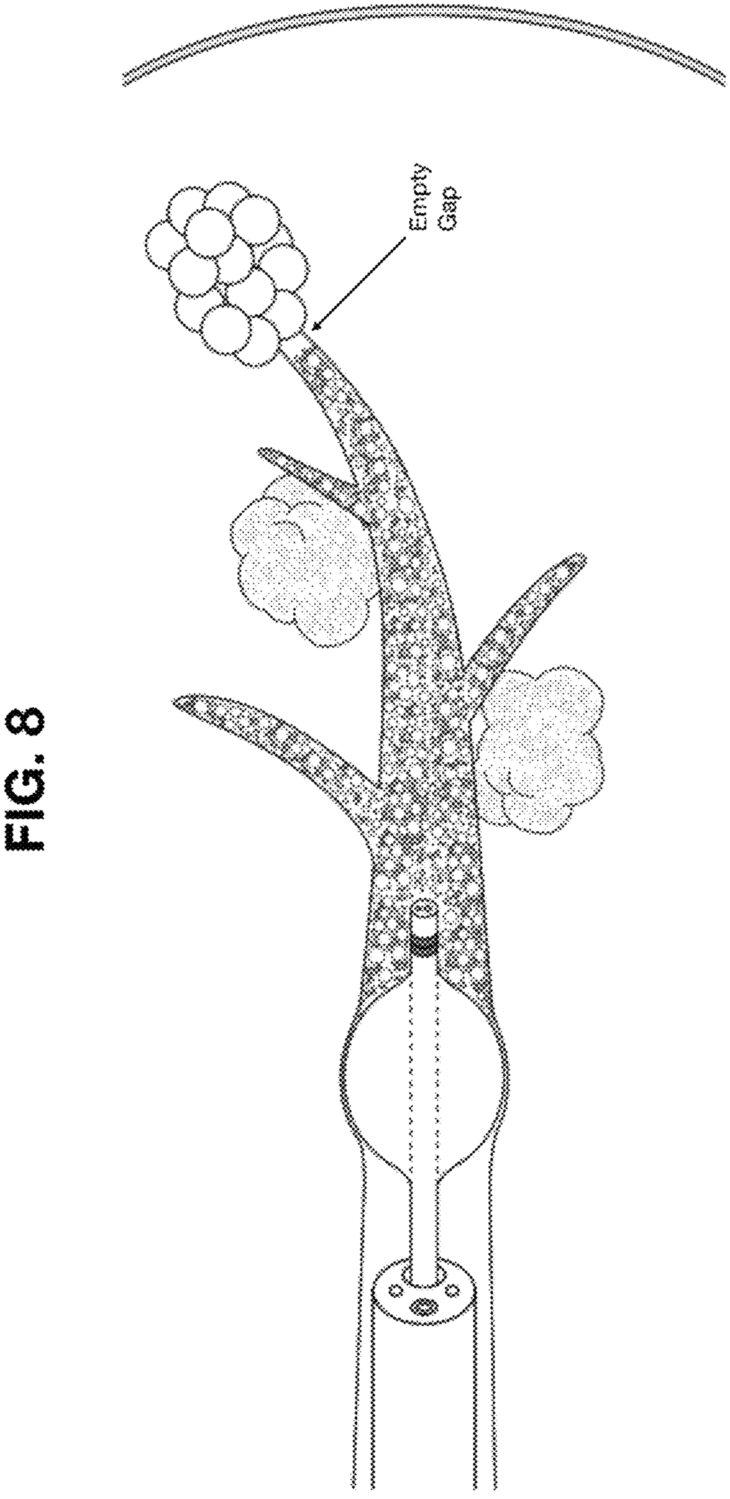
FIG. 8 shows the step of completing the instilling of the liquid metal.

In the above method, the organ is the lung of the patient (FIG. 4), and the passageway is the bronchial airway of the lung. In the above method, the step of instilling the liquid conductive material into at least two branches of the bronchial airway (FIGS. 7A-7B and 8). In the above method, the alveoli of the bronchial airway are not filled with the liquid conductive material as indicated in the empty gap in FIG. 8.

Figures 6A, 6B:
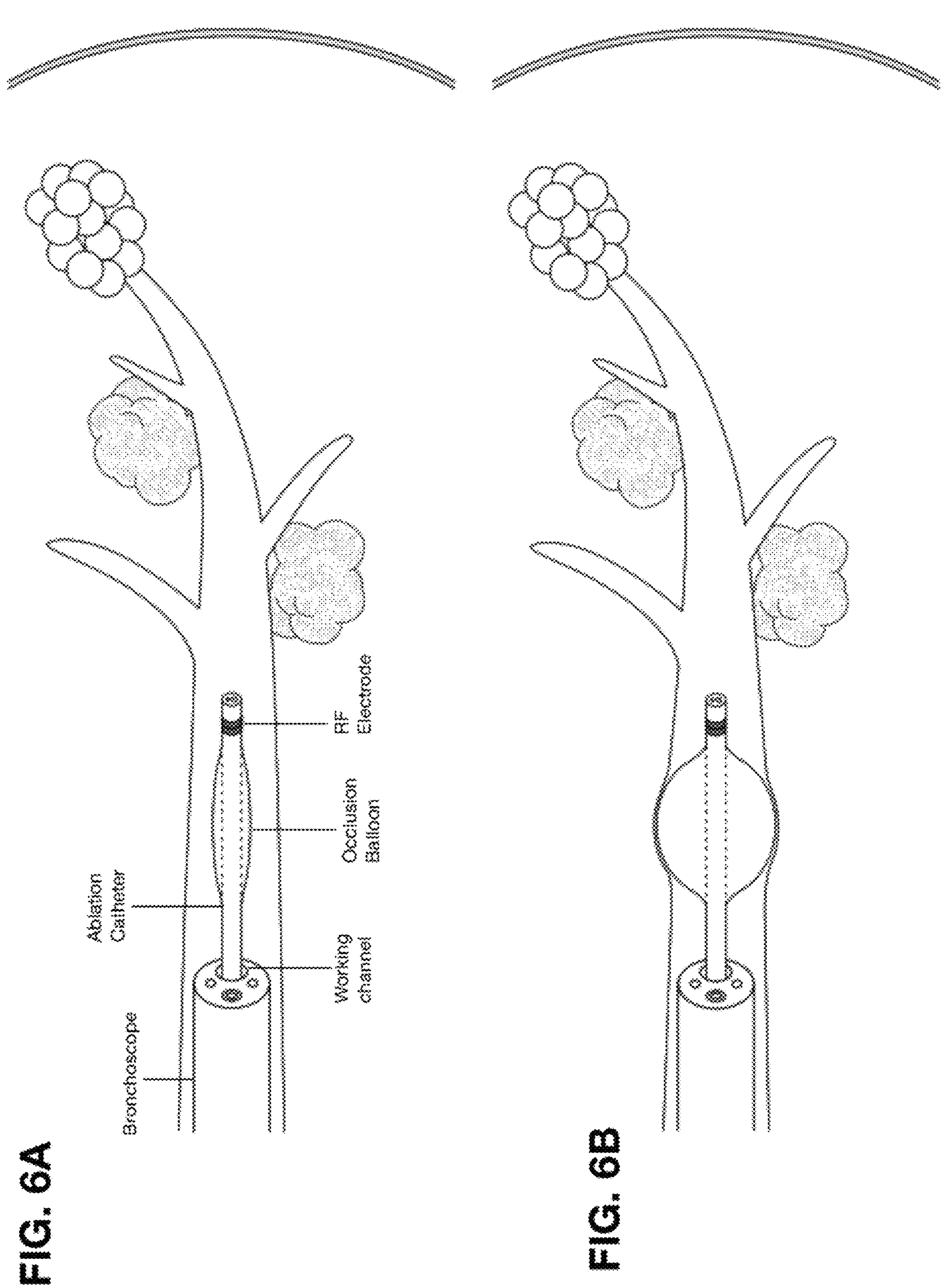
FIGS. 6A-6B shows the steps of the ablation catheter positioned at the target zone.

The above method may further comprise:

1. Having the flexible bronchoscope that comprises the instrumental channel (FIGS. 4 and 6A-6B);
2. Advancing the bronchoscope through the passageway to the target site in the body (FIGS. 4 and 6A-6B);
3. Inserting the ablation catheter device through the instrument channel of the bronchoscope (FIGS. 4 and 6A-6B); and
4. Advancing the ablation catheter device to the target site in the body organ (FIGS. 4 and 6A-6B).

Figures 11A, 11B:
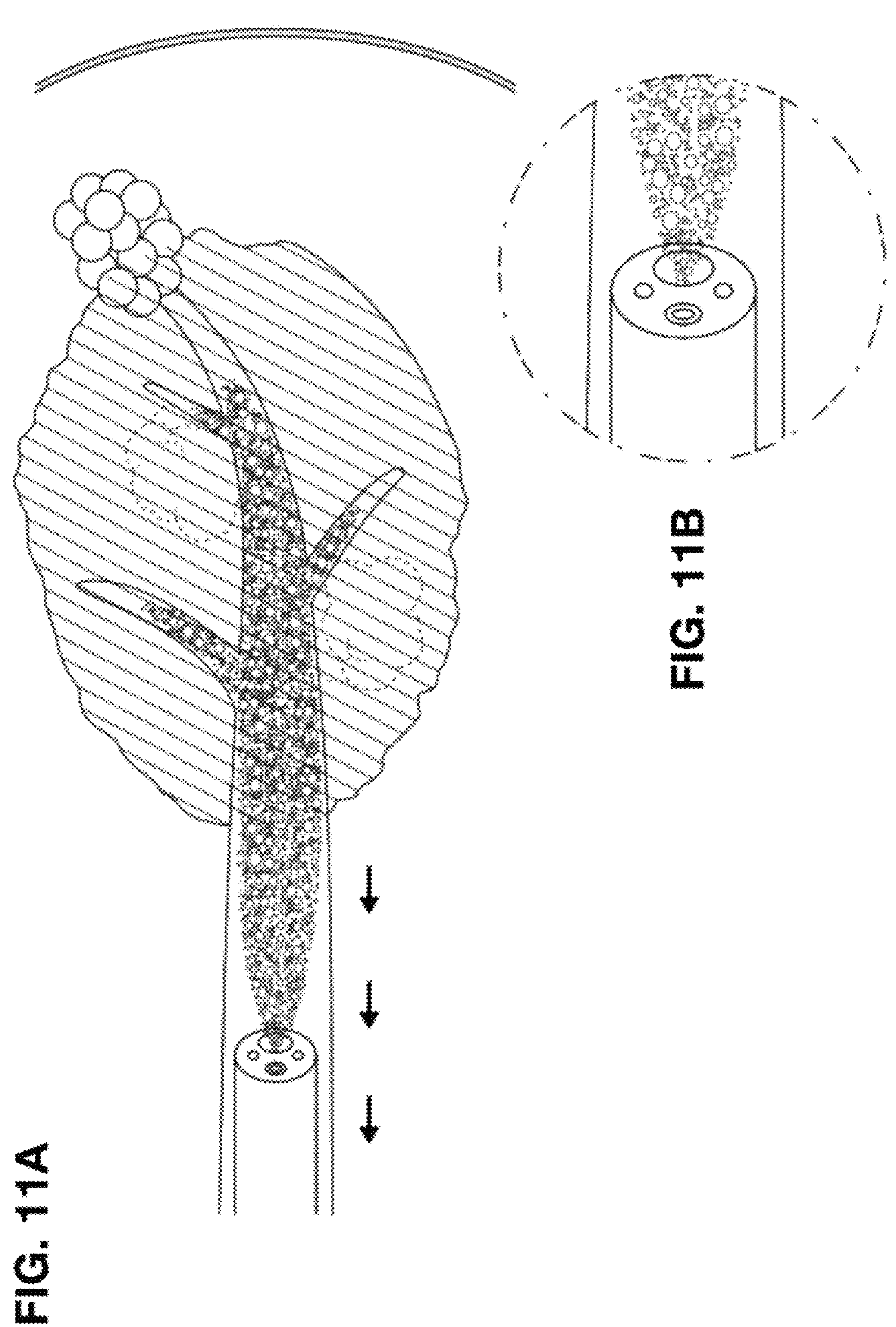
FIGS. 11A-11B shows the step of suctioning of the instilled liquid metal.

The above method may further comprise a step of aspirating the conductive material out of the passageway by suction through the bronchoscope as shown in FIGS. 11A-11B. The above method may further comprise a step of visualizing the ablation catheter device by x-ray fluoroscopy while advancing the ablation catheter device to the target site in the body organ in case of not using the bronchoscope.

The above method may further comprise a step of visualizing the liquid metal conductive material by x-ray fluoroscopy while instilling the liquid conductive material into the passageway. The above method may further comprise a step of inflating the balloon to obstruct the passageway.

In some cases, the body organ is the liver of the patient. In some cases, the body organ is the pancreas of the patient. In some cases, the body organ is the biliary tract of the patient.

In some cases, the volume of conductive material instilled may be less than 2.0 ml. In the above method, the liquid conductive material may be a mixture that further comprises indium. In some cases, the conductive material may be instilled only into the bronchial airways having a diameter of less than 9 mm. In some cases, the conductive material may be instilled only into the bronchial airways having a length of less than 10 cm.

In some cases, the conductive liquid material may not be instilled into any of the left main bronchus, the left upper lobe bronchus, the left lower lobe bronchus, the right main bronchus, the right upper lobe bronchus, the right middle lobe bronchus, or the right lower lobe bronchus. In some cases, the conductive liquid material is not instilled into any of the segmental bronchi.

Conductive Liquid Material

For a more clearly defined herein, the material could be stated as being a "conductive liquid material." The conductive liquid material comprises one or more conductive metals in liquid form. Examples of liquid metals include gallium, indium, and tin. In some embodiments, the conductive liquid material comprises gallium. In some embodiments, the conductive liquid material comprises indium. In some embodiments, the conductive liquid material comprises a mixture of liquid metals, such as a combination of gallium, indium, and tin. One such example is "Galinstan," which is an alloy of gallium, indium, and tin. Another example is "eGaIn," which is an alloy of gallium (75.5%) and indium (24.5%).

The conductive liquid material may be mostly or entirely made up of the liquid metal(s). In some embodiments, the conductive liquid material contains less than 15% (by volume) of any other materials, such as saline or water. In some embodiments, the conductive liquid material contains essentially no saline or water.

Preferred Ablation Zone

Figure 12A:
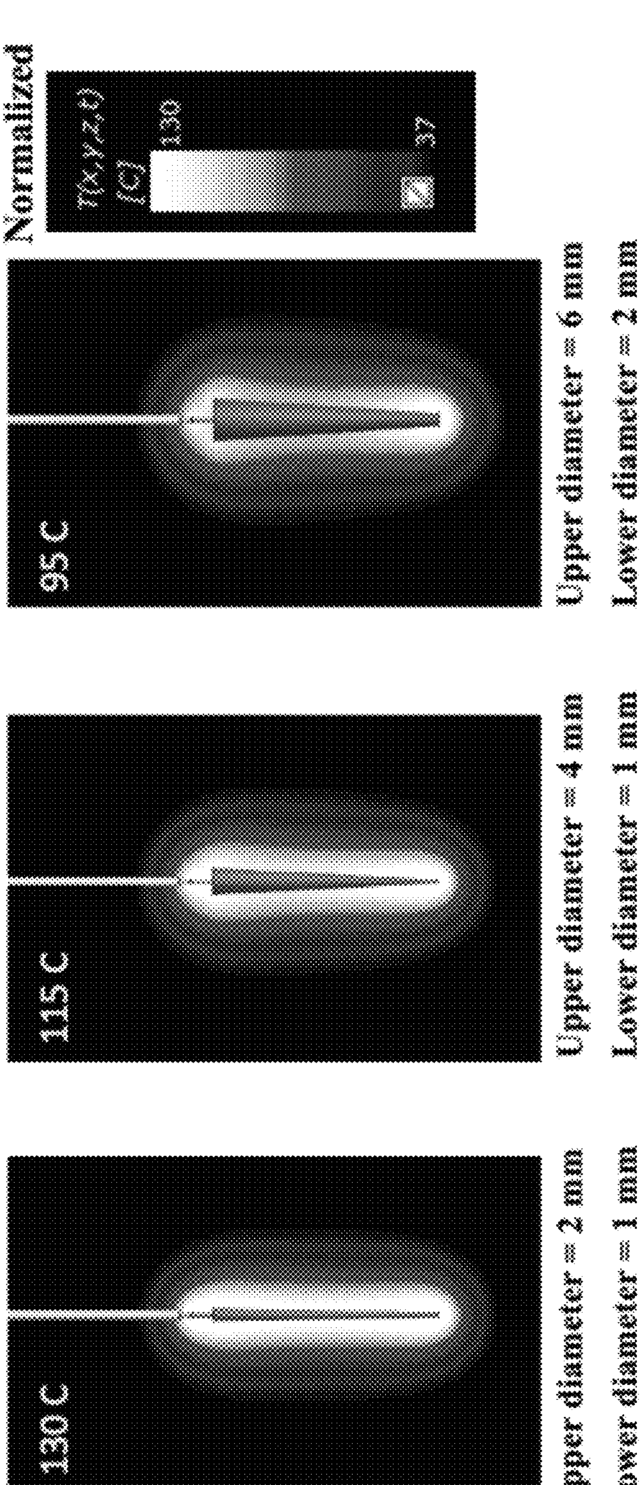
FIG. 12A shows comparison results depending on the various diameters of the branches.
Figure 13A:
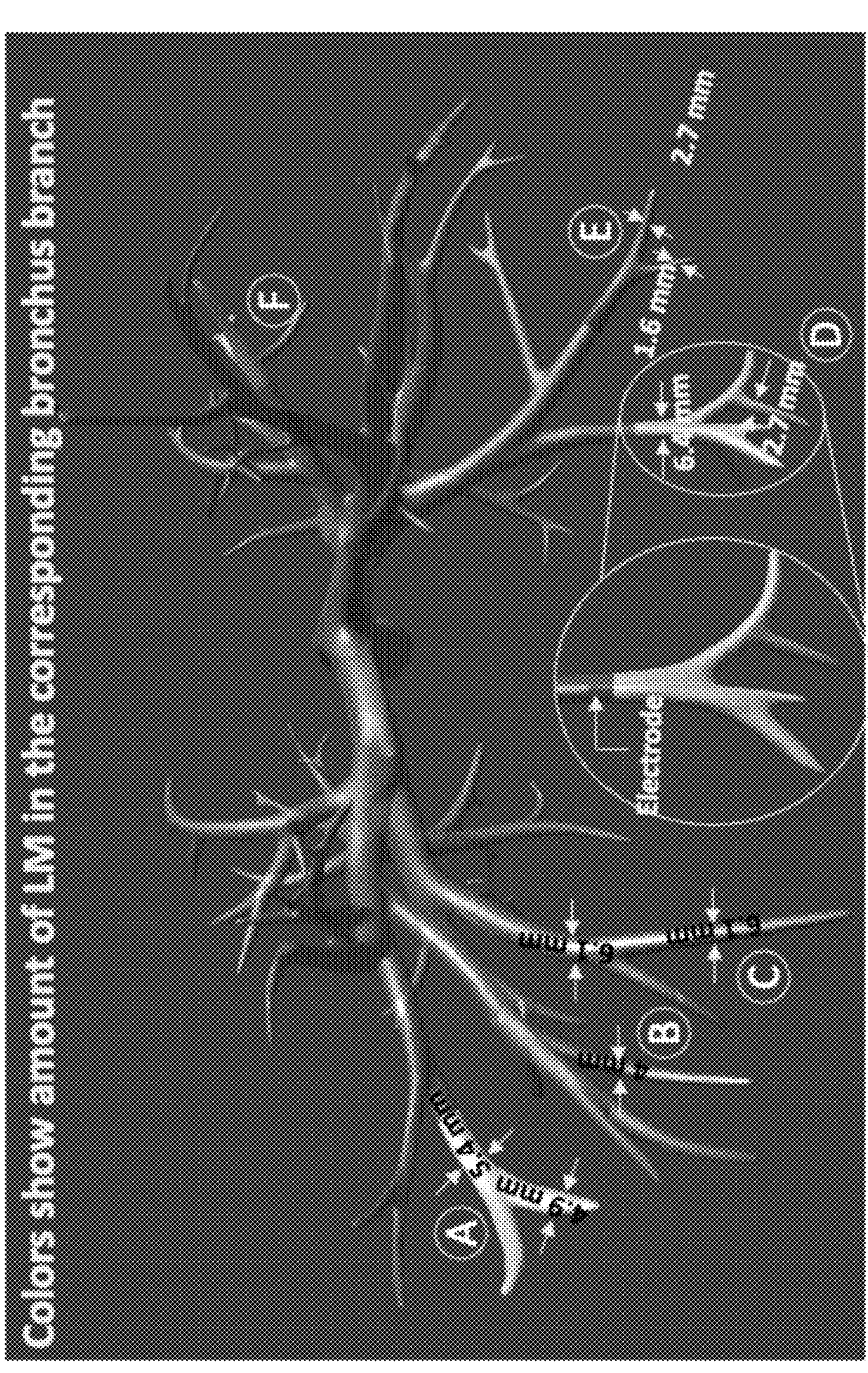
FIGS. 13A-13B shows various branches with different dimensions and corresponding ablation area results.
Figure 13B:
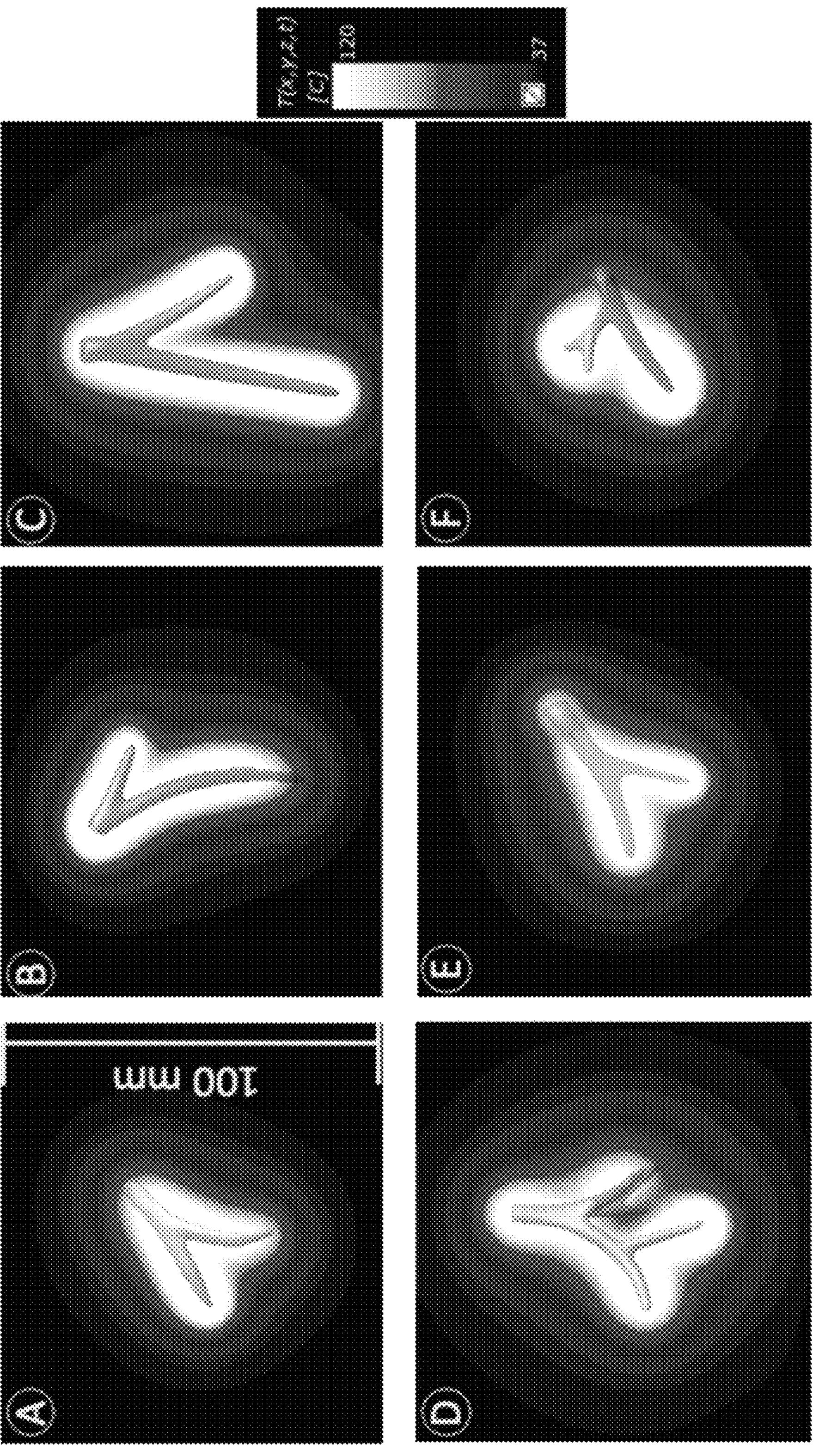

The preferred ablation zone is where smaller branches of airways which may have at least two sub-branches in the generally peripheral legion of the lung as shown in FIG. 4. For example, as shown in FIG. 12A, the branches less than 2 mm in diameter show a higher temperature. In addition, FIG. 12B shows the ablation comparisons between the bronchus without sub-branches and the bronchus with sub-branches. The results show the bronchus with sub-branches has a better ablation area as shown in FIG. 12B. FIG. 13A shows various preferred ablation zones in the peripheral lung legion. Each branch that has various dimensions shows its corresponding ablation results in FIG. 13B.

Preferred Ablation Area

Figures 5A, 5B:
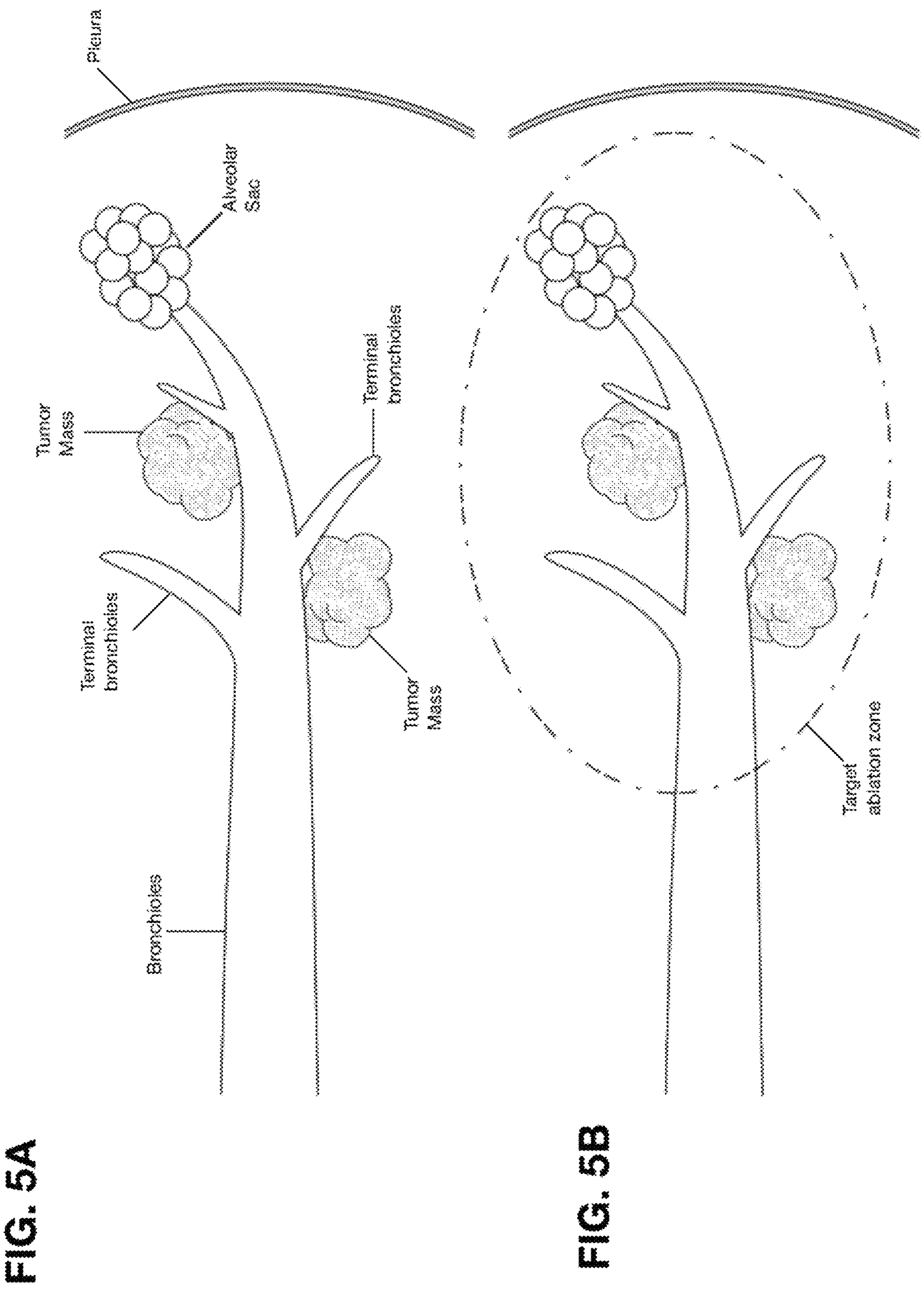
FIG. 5A shows the target ablation site in the peripheral legion.
FIG. 5B shows the preferred ablation zone.
Figure 5C:
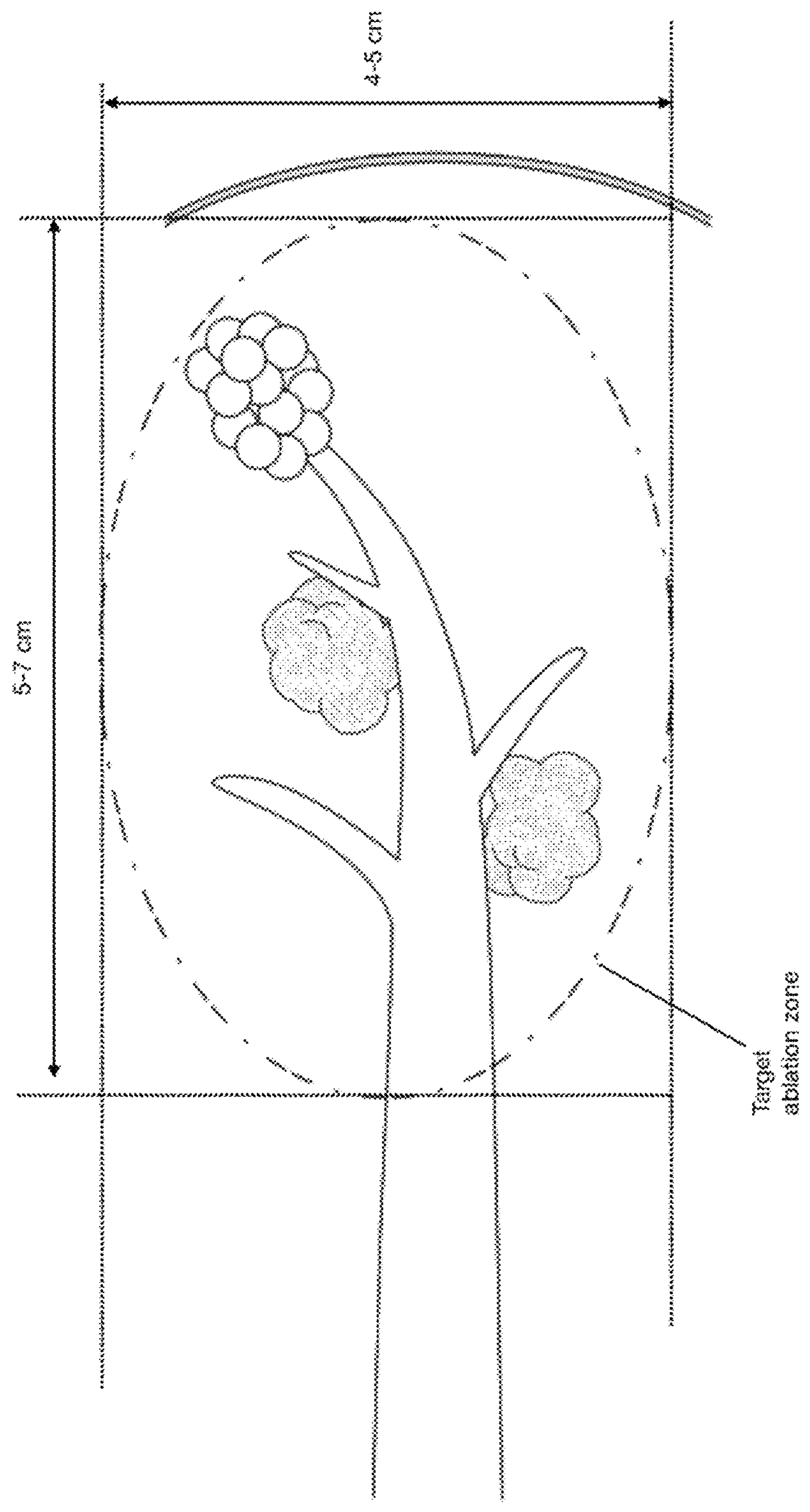
FIG. 5C shows the preferred ablation area.

In some embodiments, the preferred ablation area is defined as shown in FIGS. 5B-5C. The preferred ablation area can be adjusted depending on the infused amount of the liquid metal and the anatomy of the sub-branches of the bronchus. In some embodiments, the preferred ablation zone may be spherical or oval where, for example, the longest diameter of the zone may be about 7 cm and the shortest diameter of the zone may be about 4 cm, and the longest vertical diameter may be about 5-7 cm. In some embodiments, for this preferred ablation area, the amount of conductive liquid material (i.e., eGaIn) instilled may be less than 1.0 ml.

Again, this technique may be more useful when only smaller bronchial airways are filled with the conductive liquid material. In some embodiments, the conductive liquid material is instilled only into bronchial airways having a diameter of less than 4 mm. In some embodiments, the conductive liquid material is instilled only into bronchial airways having a length of less than 60 mm. In some embodiments, the conductive liquid material is not instilled into any of the left main bronchus, left upper lobe bronchus, left lower lobe bronchus, right main bronchus, right upper lobe bronchus, right middle lobe bronchus, or right lower lobe bronchus.

In some embodiments, the conductive liquid material is not instilled into any of the segmental bronchus, i.e., bronchi that branch directly off a lobar bronchus and are directed to a segment of the lung. For the left upper lobe of the left lung, these include the bronchi for the apicoposterior segment, anterior segment, superior lingular segment, and inferior lingular segment. For the left lower lobe of the left lung, these include the bronchi for the superior segment, anteromedial segment, lateral segment, and posterior segment. For the right upper lobe of the right lung, these include the bronchi for the apical segment, posterior segment, and anterior segment. For the right middle lobe of the right lung, these include the bronchi for the lateral segment and medial segment. For the right lower lobe of the right lung, these include the bronchi for the superior segment, medial segment, anterior segment, lateral segment, and posterior segment.

Injection Methods

FIG. 5A shows a portion of the bronchial airways where two tumor masses are located. The tumor masses are being treated by the RF ablation technique of this invention. Shown here is a bronchoscope with an ablation catheter being delivered into a trunk bronchiole near the tumor masses (FIG. 4). With the occluding balloon of the ablation catheter inflated (FIGS. 6A-6B), the gallium/indium liquid is instilled into the bronchioles (FIGS. 7A-7B). The gallium/indium liquid is delivered out of the fluid channel of the RF ablation catheter. The gallium/indium liquid goes into the trunk bronchiole as well as at least two (three) branches of the trunk bronchiole. Note however that the gallium/indium liquid does not go into the alveolar sac as shown in FIG. 8. This is to avoid damage to the pleura which is close to the alveolar sac. Thus, there is a small gap at the terminus of the bronchiole that does not contain gallium/indium liquid.

The method comprises injecting the conductive liquid material in the manner described herein. In some embodiments, the conductive liquid material is not instilled into any alveoli of the lung. The volume of the conductive liquid material may depend on various factors, such as the size of the tumor, location of the tumor, number of branches, etc. In some embodiments, the amount of conductive liquid material instilled is less than 2.0 ml; in some cases, less than 1.0 ml; and in some cases, less than 0.5 ml. In some embodiments, at least two (three) bronchiole branches of the bronchial airways are instilled with the conductive liquid material; and in some cases, at least five bronchiole branches.

RF Operating Parameter

There are various operating parameters that could be selected to achieve the desired ablation result. The RF power (watts) is applied to maintain a suitable ablation temperature in the ablation zone. The ablation temperature could be monitored via a temperature sensor located on the ablation catheter. In some embodiments, the ablation temperature is at least 60° C.; and in some cases, at least 80° C. In some embodiments, the ablation temperature is maintained for at least 7 minutes; and in some cases, up to a maximum of 30 minutes.

The RF power needed for the ablation temperature could be in the range of 40-180 watts. The total amount of RF energy applied will vary depending on factors such as the power (watts) being applied and the duration of time. In some embodiments, the total (accumulated) RF ablation energy applied for the treatment is in the range of 40-250 kW·s; and in some cases, in the range of 70-170 kW·s of total RF power applied.

The descriptions and examples given herein are intended merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

The invention claimed is:

1. A method of treating a tumor in a patient, comprising:
having a liquid metal that comprises gallium;
filling and containing a volume of the liquid metal within the bronchial airway such that the liquid metal forms an electrically continuous metallic body;
electrically coupling an RF energy source directly to the liquid metal such that the liquid metal forms the active RF electrode for ablating the lung tumor;
applying an RF current to the liquid metal; and
removing the liquid metal from the bronchial airway after ablation.

2. The method of claim 1, wherein the bronchial airway is a segmental or subsegmental bronchus.

3. The method of claim 1, wherein the step of filling and containing comprises filling and containing the liquid metal into at least three branches of the bronchial airway.

4. The method of claim 1, wherein alveoli of the bronchial airway are not filled with the liquid metal.

5. The method of claim 2, wherein the liquid metal is instilled only into bronchial airways having a diameter of less than 9 mm.

6. The method of claim 5, wherein the liquid metal is instilled only into bronchial airways having a length of less than 10 cm.

7. The method of claim 1, further comprising visualizing the ablation catheter device by x-ray fluoroscopy while advancing the ablation catheter device to the target site.

8. The method of claim 7, further comprising visualizing the liquid metal by x-ray fluoroscopy while filling and containing the liquid metal into the passageway.

9. The method of claim 1, further comprising inflating the balloon to obstruct the bronchial airway.

10. The method of claim 1, wherein the volume of the liquid metal instilled is less than 2.0 ml.

11. The method of claim 1, wherein the liquid metal is a mixture that further comprises indium.

* * * * *